US012751688B2

(12) United States Patent
Zupkas et al.

(10) Patent No.: US 12,751,688 B2
(45) Date of Patent: Oct. 6, 2026

(54) ULTRASOUND VISUALIZATION DEVICE

(71) Applicant: THE REGENTS OF THE UNIVERSITY OF CALIFORNIA, Oakland, CA (US)

(72) Inventors: Paul Zupkas, San Diego, CA (US); Roger Sur, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 840 days.

(21) Appl. No.: 18/024,676

(22) PCT Filed: Sep. 7, 2021

(86) PCT No.: PCT/US2021/049308
§ 371 (c)(1),
(2) Date: Mar. 3, 2023

(87) PCT Pub. No.: WO2022/051725
PCT Pub. Date: Mar. 10, 2022

(65) Prior Publication Data

US 2023/0309951 A1 Oct. 5, 2023

Related U.S. Application Data

(60) Provisional application No. 63/074,822, filed on Sep. 4, 2020.

(51) Int. Cl.
*A61B 8/00* (2006.01)
*A61B 8/08* (2006.01)
*A61B 17/34* (2006.01)

(52) U.S. Cl.
CPC ........ *A61B 8/0841* (2013.01); *A61B 17/3403* (2013.01); *A61B 17/3478* (2013.01); *A61B 2017/3413* (2013.01)

(58) Field of Classification Search
CPC ............ A61B 17/3403; A61B 17/3478; A61B 2017/3413; A61B 2090/3925; A61B 2217/007; A61B 8/0841
See application file for complete search history.

(56) References Cited

U.S. PATENT DOCUMENTS

2007/0197954 A1 8/2007 Keenan
2010/0114031 A1 5/2010 Jarial et al.
(Continued)

FOREIGN PATENT DOCUMENTS

WO 2009157289 A1 12/2009
WO 2020175995 A1 9/2020

OTHER PUBLICATIONS

Howlett, J., Groote Schuur Hospital, University of Cape Town, Dept of Urology; Eau 2018: SabreSource: A Novel Percutaneous Nephrolithotomy Apparatus to Aid Collecting System Puncture—A Preliminary Report, Mar. 16-20, 2018.
(Continued)

*Primary Examiner* — Mark D Remaly
(74) *Attorney, Agent, or Firm* — Eleanor Musick; Torrey Pines Law Group PC

(57) ABSTRACT

An assembly for facilitating ultrasonic visualization of positioning of a needle inserted into tissue includes a needle that is inserted into a sheath to define a transport channel between an outer surface of the needle and an inner surface of the sheath for transport of a fluid that is introduced into the sheath. The transport channel includes features that induce formation of ultrasonically visible features from the fluid. These features exit from the end of the sheath where they can be detected via ultrasonic imaging.

34 Claims, 6 Drawing Sheets

(56) References Cited

U.S. PATENT DOCUMENTS

| | | | | |
|---|---|---|---|---|
| 2014/0257090 | A1 | 9/2014 | Fischer, Jr. et al. | |
| 2021/0196341 | A1* | 7/2021 | Rajagopalan .......... | A61B 18/20 |

OTHER PUBLICATIONS

Howlett, J., SabreSource TM: a novel percutaneous nephrolithotomy apparatus to aid collecting system puncture—a preliminary report; SAJS, Jun. 2020, pp. 105a-105d, vol. 58, No. 2.

Iordache, A., Ultrasound for kidney access in percutaneous nephrolithotomy: a contemporary review, Med Ultrason 2018, pp. 508-514, vol. 20, No. 4.

Lazarus, J., Optically tracked needle for ultrasound guided percutaneous nephrolithotomy (PCNL) puncture: A preliminary report, Journal of Endourology, Jun. 11, 2021, (3 pages) vol. 0.

Tenant, Sean C., et al., The clinical use of contrast-enhanced ultrasound in the kidney, Ultrasound 24(2) pp. 94-103.

* cited by examiner

ULTRASOUND VISUALIZATION DEVICE

RELATED APPLICATIONS

This application is a 371 national stage filing of International Application No. PCT/US2021/049308, filed Sep. 7, 2021, which claims the benefit of the priority of U.S. Application No. 63/074,822, filed Sep. 4, 2020, each of which is incorporated herein by reference in its entirety.

FIELD OF THE INVENTION

The present invention relates to an assembly for guiding positioning of a needle tip within tissue by enhancing the sensitivity of ultrasound visualization and more particularly to an assembly improving the accuracy of renal puncture procedures.

BACKGROUND

Percutaneous nephrolithotomy (PCNL) is standard of care for large renal stone burdens such as >20 mm. Renal collecting system puncture is a critical step in PCNL as it gives the surgeon access to the kidney stone in a minimally invasive method. While fluoroscopy has been the puncture technique of choice, adoption has been limited because obtaining a perfect puncture is technically challenging. PCNL is considered an "advanced" endourological procedure that only 27% of American urological surgeons trained in PCNL continue to use, with only 11% of American urologists performing PCNL routinely themselves. Instead, the renal puncture access is relegated to radiologists, and although radiologists are able to gain access, their involvement complicates the procedural logistics and, theoretically, adds morbidity through the employment of a second, separate procedure.

When the renal puncture is performed by the urologist, it is commonly performed simultaneously as part of the PCNL procedure. Fluoroscopic guidance is the primary technique used since the 1970's. More recently, the introduction of ultrasound assisted renal puncture has become more commonplace. See, e.g., Iordache, A., et al., *Med Ultrason* 2018, 20(4): 508-14). Benefits of ultrasound assisted renal puncture include absence of ionizing radiation for both patient and provider, ability to identify other organs (minimizing complications), and easier appreciation of the posterior calyx. (Usawachintachit, M., et al., *J Endourol* 2016 30(8).)

Despite these advantages, there is a reticence to adoption of ultrasound assisted renal puncture. In addition to having to learn an imaging technique that most urologists are not familiar with, there is the added difficulty of visualizing the placement of the needle during the puncture. The needle has poor echogenicity and its echogenicity varies with surrounding tissue density (patients can have different tissue density). In aggregate, this adds to hesitancy to adopt a technique whose primary limitation is visualization. We therefore propose a unique needle with significantly improved visualization. The incorporation with PCNL potentially assists in the diffusion and adoption of ultrasound assisted renal puncture.

BRIEF SUMMARY

According to embodiments of the invention, a modified needle and sheath system is used to gain access to the renal calyx under ultrasound guidance. The inventive needle/sheath combination is inserted through the skin and kidney into the renal calyx. The needle is then removed and a guidewire inserted through the sheath into the renal calyx to allow access to the renal calyx of other instruments. The benefit of the inventive approach is that it allows improved visualization of the tip of the needle/sheath in the renal calyx using ultrasound as a guidance modality.

In some embodiments, the invention uses air as a means for visualization of the tip of the needle. The air or ultrasound contrast media, such as perflutren, is injected in a chamber at the distal end of the needle/sheath and forced through the sheath over the needle to exit the sheath at the end of the needle. Air bubbles are very echogenic—the bubbles exiting the end of the sheath provide an ultrasonically visible landmark.

Features of the invention include a chamber at the distal end of the needle/sheath that allow injection of air. The chamber is located at the distal end of the sheath, but the needle passes through the chamber and is sealed to form an fluid tight seal at the end of the needle sheath combination. The fluid tight feature of the needle to the chamber is critical as it forces the air/contrast media injected into the chamber to exit at the distal end of the needle/sheath. Although the seal between the needle and chamber must be fluid tight, it must also allow the needle to be removed from the chamber to allow a guidewire to be inserted through the chamber and sheath, into the renal calyx. The introduction of air/media into the chamber may be accomplished manually, such as by using a syringe, or automatically using equipment that could supply a metered dose of air or contrast media.

Another feature of the inventive system is the shape of the needle in the chamber and the sheath. The needle is shaped to allow air/fluid flow along its length in the sheath. The normal gap defined between needle and sheath is narrow enough to restrict transport of air/fluid to the proximal end of the needle/sheath. The normally cylindrical needle may be modified to remove a portion of the needle, for example, by flattening a portion of the needle or machining a longitudinal channel along the length the needle. At the distal end of the sheath, where the needle may extend a short distance to end in a point. Additional modification of the needle may include, for example, an annular channel formed near the distal end may enhance uniform radial distribution of air/media at the end of the sheath. Further modifications may include grooves emanating from the annular channel. inside the sheath. Selection of the size/depth of the grooves provide control of the size of the bubbles generated at the end of the sheath.

In a first aspect of the invention, an assembly for facilitating ultrasonic visualization of positioning of a needle inserted into tissue includes a needle having a needle length; a sheath having a sheath length and configured for concentrically receiving the needle, the sheath having a sheath head disposed at a proximal end configured for introducing fluid into a transport channel defined between an outer surface of the needle and an inner surface of the sheath, where the transport channel includes features configured for inducing formation of ultrasonically visible features at a distal end of the sheath; and a fluid source in fluid communication with the sheath head for introducing fluid under pressure. In some embodiments, the transport channel comprises at least one longitudinal channel formed in the inner surface of the sheath. The at least one longitudinal channel may be a plurality of longitudinal channels extending along the sheath length. These longitudinal channels may be defined by ribs extending radially inward from the inner surface of the sheath. In another implementation, the at least one longitudinal channel are a plurality of longitudinal channels shorter than the sheath length disposed near the distal end of the sheath. The sheath may include a plurality of radial openings located near a distal end of the sheath. In still other embodiments, the transport channel may be at least one longitudinal channel formed in an outer surface of the needle. In some configurations, the at least one longitudinal channel may extend a partial length of the needle to intersect with an annular channel configured to direct the fluid radially outward from the needle. The annular channel may be disposed at a position along the needle length corresponding to the distal end of the sheath, or it may be disposed at a position along the needle length that is less than the full sheath length, and the sheath may have a plurality of radial openings disposed to align with the annular channel. The annular channel may be disposed at a position along the needle length that is less than the full sheath length, and wherein the sheath may have a plurality of tapered grooves formed on the inner surface, where each groove has a first end that aligns with the annular channel and a second end that extends to the distal end of the sheath. A plurality of tapered grooves may be disposed near a distal end of the needle, where the tapered grooves extend distally from the annular channel.

In some embodiments, the longitudinal channel may be formed by flattening a side of the needle or by forming a groove in the outer surface of the needle. In most embodiments, the needle length is greater than the sheath length. The fluid may be air or a contrast media suspension.

In another aspect of the invention, a method for visualizing positioning of a needle inserted into tissue, comprising inserting into a target tissue the assembly described above, and using an ultrasonic imaging instrument to generate an image of ultrasonically visible features at the distal end of the sheath.

In still another aspect of the invention, an assembly for facilitating ultrasonic visualization of positioning of a needle inserted into tissue includes: a sheath having a hollow tubing having a sheath length and a sheath end, the sheath having a sheath head disposed at a proximal end configured for introducing fluid into the sheath; a needle concentrically disposed within the sheath to define a transport channel between an outer surface of the needle and an inner surface of the sheath, wherein the transport channel comprises features configured for inducing formation of ultrasonically visible features at a distal end of the sheath; and a fluid source in fluid communication with the sheath head for introducing fluid under pressure. In some embodiments, the transport channel comprises at least one longitudinal channel formed in the inner surface of the sheath. The at least one longitudinal channel may be a plurality of longitudinal channels extending along the sheath length. These longitudinal channels may be defined by ribs extending radially inward from the inner surface of the sheath. In another implementation, the at least one longitudinal channel are a plurality of longitudinal channels shorter than the sheath length disposed near the distal end of the sheath. The sheath may include a plurality of radial openings located near a distal end of the sheath. In still other embodiments, the transport channel may be at least one longitudinal channel formed in an outer surface of the needle. In some configurations, the at least one longitudinal channel may extend a partial length of the needle to intersect with an annular channel configured to direct the fluid radially outward from the needle. The annular channel may be disposed at a position along the needle length corresponding to the distal end of the sheath, or it may be disposed at a position along the needle length that is less than the full sheath length, and the sheath may have a plurality of radial openings disposed to align with the annular channel. The annular channel may be disposed at a position along the needle length that is less than the full sheath length, and wherein the sheath may have a plurality of tapered grooves formed on the inner surface, where each groove has a first end that aligns with the annular channel and a second end that extends to the distal end of the sheath. A plurality of tapered grooves may be disposed near a distal end of the needle, where the tapered grooves extend distally from the annular channel.

In some embodiments, the longitudinal channel may be formed by flattening a side of the needle or by forming a groove in the outer surface of the needle. In most embodiments, the needle length is greater than the sheath length. The fluid may be air or a contrast media suspension.

DETAILED DESCRIPTION OF EMBODIMENTS

The inventive needle and sheath assembly facilitates visualization to allow accurate placement of the sheath tip within tissue via ultrasonic imaging. In some applications, the assembly is used to introduce air into the tissue where it forms bubbles at the sheath tip. In other applications, an ultrasound contrast media, for example, perflutren, a suspension of lipid microspheres, i.e., particles, is transported by the assembly for release at the sheath tip. With either material, the bubbles of air or particles of contrast media are highly echogenic, producing an ultrasonically visible landmark at their location at the end of the sheath. For purposes of this disclosure, the term "fluid means the air or contrast media suspension that is transported by the assembly. "Ultrasonically-visible features" are air bubbles, microbubbles, contrast media particles, masses, or similar elements that exit the sheath after manipulation of the fluid by structures within the assembly to form echogenic features (e.g., bubbles, particles, areas) within the tissue around the sheath tip which can be visualized using ultrasound.

FIGS. 1A-1D schematically illustrate the basic components of the sheath 10 and needle 20 assembly for all embodiments of the inventive device. Table 1 provides exemplary dimensions, ranges and preferred (e.g., for renal puncture), for each of these components. Note that these exemplary dimensions are not intended to be limiting. Those of skill in the art will recognize that different dimensions may be selected to meet the needs of a specific application.

Figures 1A, 1B, 1C, 1D:
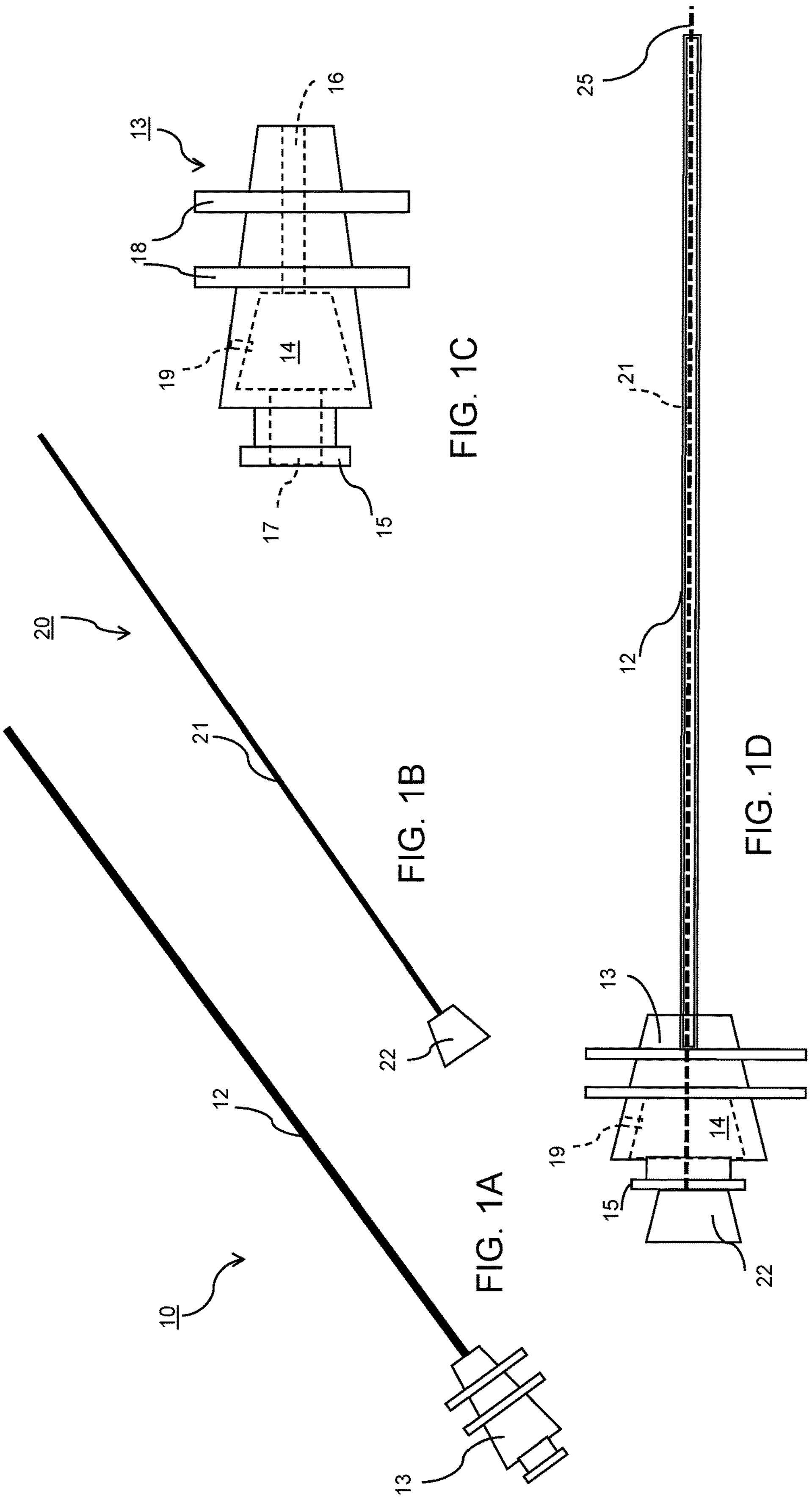
FIGS. 1A-1B diagrammatically illustrate an exemplary needle and sheath, respectively, for use with all embodiments of the inventive system.
FIG. 1C provides a more detailed view of the sheath head of FIG. 1A.
FIG. 1D illustrates an exemplary assembly of the needle and sheath.

Hollow sheath 12, shown in FIG. 1A, is a generally cylindrical rigid tube that extends from sheath head 13. The relative dimensions of the inner diameter of sheath 12 and needle 21 are selected to provide a close, substantially fluid tight fit between the two surfaces while still allowing the needle 21 to be slid into and out of the sheath freely, without significant resistance. FIG. 1B illustrates needle assembly 20, consisting of needle 21 and needle stopper 22. Either or both the needle 21 and sheath 12 may be formed from biocompatible materials, including metals, such as stainless steel, titanium, cobalt-chrome, plastics, or polymers, such as medical grades of polyvinylchloride (PVC), polyethylene, polyether ether ketone (PEEK), polycarbonate, ULTEM® polyetherimide, polysulfone, polypropylene and polyurethane, or combinations thereof.

Referring to FIG. 1C, sheath head 13 is shown as a generally frustoconical plug with a hollow chamber 14 at its proximal end that is in fluid communication with a bore 16 in its distal end that is dimensioned to receive the proximal end of sheath 12 to form a channel through which needle 21, or a guidewire, can be inserted. When inserted into bore 16, the proximal end of sheath 12 forms a fluid tight seal between its outer surface and sheath head 13. Annular ridges 18 or similar features may be formed on the outer surface of sheath head 13 to facilitate manipulation by the user and/or to act as an insertion stop. At the base (proximal) end of sheath head 13 a flanged extension 15 may be provided with a bore 17 extending therethrough and into chamber 14. Bore 15 defines an opening for insertion of the needle 21 (or guidewire) and to receive needle stopper 22. Side port 19 provides a port for introduction of air or fluid that will be used to generate the bubbles (echogenic features) for visualization. As shown in FIG. 1D, when inserted into bore 17, stopper 22 closes chamber 14 to form a fluid tight seal. While needle stopper 22 is illustrated as simple frustoconical plug, typically formed of an appropriate elastomeric material, with a distal end that inserts into bore 17 to form a substantially fluid-type seal, other connections may be used, for example, a plug with external threads to mate with internal threads within bore 17, a Luer lock attachment, or other conventional releasable connectors may be used. As will be readily apparent to those in the art, other shapes may be used for sheath head, e.g., cylindrical or a flattened slab, and external features may be varied, e.g., knurled surfaces or thumb/finger holds (ridges or depressions) may be provided to enhance the user's ability to grip and maneuver the assembly.

TABLE 1

| Component/ Dimension | Sheath | Sheath Head | Needle |
|---|---|---|---|
| Length | 127-222.3 mm (5-8.75 in.) pref. 155.6 mm (6.125 in.) (from end of head) | 19-38 mm (0.75-1.5 in.) pref.: 22.2 mm (0.875 in,) | 127-305 mm (5-12 in.) pref.: 184.15 mm (7.25 in) |

TABLE 1-continued

| Component/ Dimension | Sheath | Sheath Head | Needle |
|---|---|---|---|
| Outer Diameter | 1.02-2.03 mm (0.040-0.080 in.) pref.: 1.27 mm (0.050 in) | varied | 0.64-1.65 mm (0.025-0.065 in.) pref.: 0.89 mm (0.035 in) |
| Inner Diameter | 0.62-1.63 mm (0.023-0.063 in.) pref.: 0.91 mm (0.036 in.) | varied | N/A |
| Wall thickness | 0.125-0.5 mm (0.005-0.020) pref.: 0.18 mm (0.007 in.) | N/A | N/A |

As illustrated in FIG. 1D, the distal end 25 of needle 21 extends beyond the sheath end. An exemplary extension will be on the order of 1.25-5 mm (0.05-0.20 in.), with a preferred extension of 3.2 mm (0.125 in.).

Figure 2:
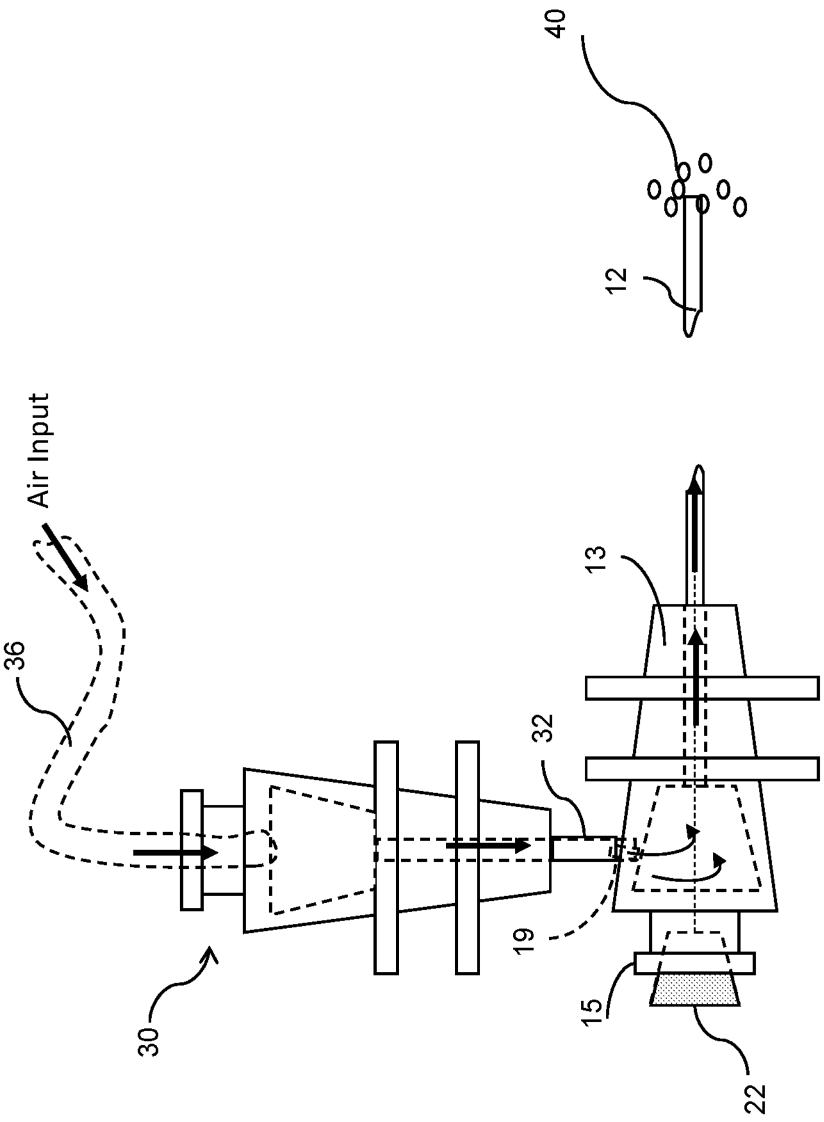
FIG. 2 illustrates an assembly for introducing air or fluid into the sheath head according to an embodiment of the invention.

Referring to FIG. 2, an exemplary assembly for introducing fluid into sheath head 13 is shown. Injector head 30 (which is illustrated having a similar configuration to sheath head 13 for convenience) is connected to fluid line 36 through which (lightly) pressurized fluid is introduced. The pressurization may be applied manually via a syringe or automatically (or semi-automatically) using a metered pump with appropriate pressure regulation. A cannula 32 or similar structure extending from the distal end of injector head 30, is inserted into side port 19 of sheath head 13. The dimensions of port 19 should closely fit the outer dimensions of cannula 32 to provide a fluid tight seal to prevent loss of pressure. This may be achieved by lining port 19 with a soft, resilient material, e.g., silicone, that is compressible to expand the opening when cannula 32 is inserted to produce a sufficiently tight fit to create a seal without providing so much resistance to removal of the cannula that the user risks moving the sheath from the target position. In some embodiments, sheath head 13 may itself be formed of a resilient plastic or polymer (medical grade) that will compress to allow the cannula to be easily inserted and will resile to self-seal once the cannula is withdrawn. In another embodiment, injector head 30 may be integrally formed with sheath head 13, e.g., molded as a single unit. In this configuration, the cannula 32 may be a molded tube or channel that provides fluid communication from the injector head to the sheath head. This embodiment can incorporate a one-way valve in injector head 30 to prevent regression of fluid through sheath head 30 should the fluid line 36 become disconnected from the injector head 30. With needle assembly 20 inserted into the sheath assembly, needle stopper 22 seals the proximal end of sheath head 13, causing the fluid introduced through port 19 to be forced into sheath 12. Structures defined by the combination of the interior of sheath 12 and the outer surface of needle 21, which will be described in more detail below, cause the fluid to break up into bubbles 40 (or other echogenic features) that exit near the end of sheath 12. These bubbles enable the ultrasound visualization of the distal end of the sheath for precise positioning.

The structures and relationships shown in and described with reference to FIGS. 1A-1D and 2 are common to all embodiments. Also common to all embodiments is the use of the combination of the inner surface of the sheath and the outer surface of the needle to define a transport pathway that is configured to generate bubbles from the fluid as it moves through the pathway and exits near the end of the sheath. In some embodiments, the sheath may have small radial openings, on the order of 0.1 to 0.5 mm, formed through the sheath sidewalls at a short distance, e.g., 3-5 mm (0.125 in.), from the tip so that the bubbles exit through the openings. In other embodiments, the bubbles follow channels defined within the transport pathway. These channels may be formed on the inner surface of the sheath, the outer surface of the needle, or a combination of both.

Figure 3:
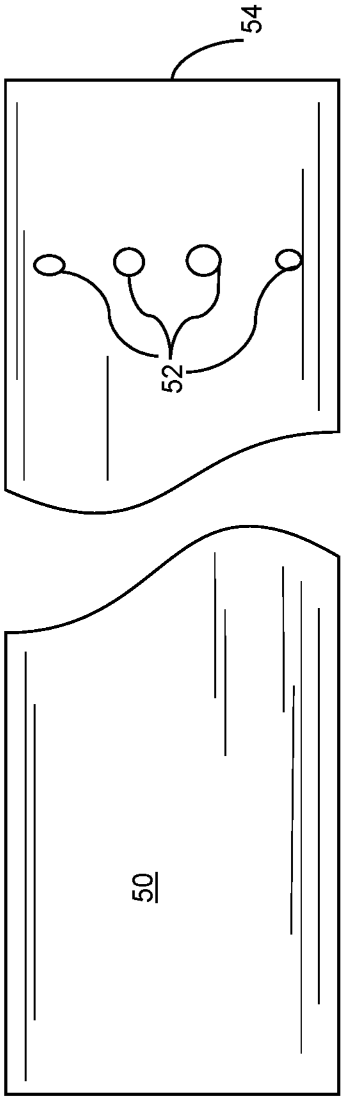
FIG. 3 is a side plan view of a sheath according to a first embodiment of the invention.

The injection occurs at the proximal end of the sheath body and the fluid travels along the length of the needle and interior of the sheath to exit the distal end of the needle/sheath combination. FIG. 1D illustrates a basic starting structure for all embodiments, which does not involve any surface modification of either the needle or inner surface of the sheath. In this configuration, the spacing between the outer surface of needle 21 and the inner surface of sheath 12 should generally be too thin to allow any appreciable fluid to pass through the sheath. However, it may be possible depending on the fluid characteristics (viscosity) to form a spacing that is thin enough to prevent laminar flow and instead induce turbulent flow to break up the fluid into small particles that will exit the sheath tip. In some embodiments, breakup of the flow into bubbles can be facilitated by using a sheath configuration such as that shown in FIG. 3. In this implementation, sheath 50 is dimensioned similar to sheath 12, however, radial openings 52, about 0.1 to 0.5 mm in diameter, may be formed in a ring through the walls of the sheath approximately 3-5 mm from the sheath tip 54 to allow the fluid to escape through the openings as bubbles. In this approach, it may be helpful to have a slightly larger diameter at the end of the needle to ensure that the fluid is forced out of the openings 52.

Figure 4A:
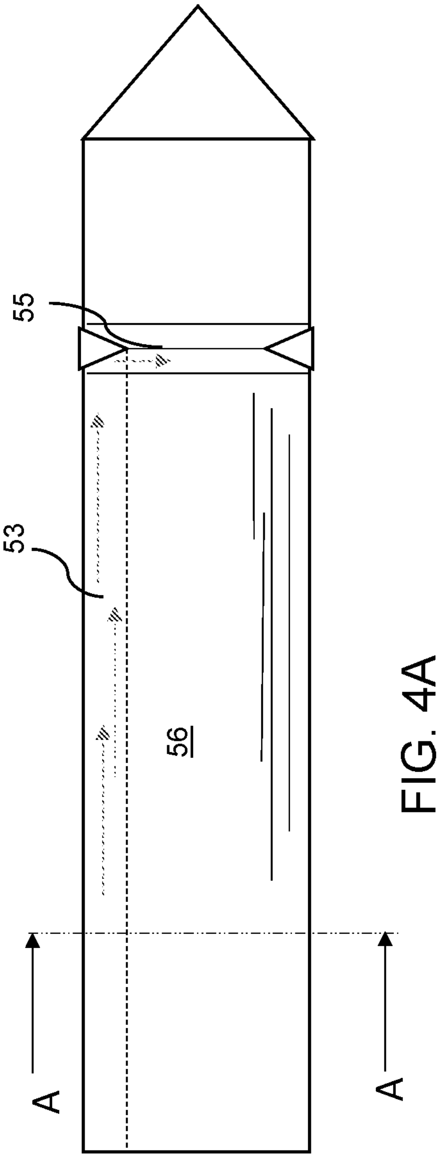
FIG. 4A is a side plan view of a needle according to a first embodiment.
Figure 4B:
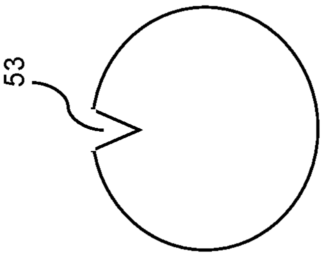
FIG. 4B is a cross-sectional view taken along line A-A of FIG. 4A.

FIGS. 4A-4B illustrate an embodiment of a needle 51 in which a longitudinal channel or groove 53 is formed along the partial length of the needle to a point at which it intersects with annular channel or groove 55. When needle 51 is inserted into sheath 50, groove 55 aligns lengthwise with the ring of openings 52 in sheath 50, so that fluid is guided from channel 53 to channel 55 and radially outward to pass through openings 52. It should be noted that openings 52 need not be formed in a straight line annulus but can be slightly staggered to distribute the bubbles (or echogenic features). While grooves 53 and 55 are illustrated with a V-shaped cross-section, this is intended to be exemplary only. It will be appreciated by those in the art that a U-shaped, square-shaped, or other shaped cross-section channel can be used to transport the air/fluid down the length of the sheath and out the openings 52 in the sheath. Exemplary dimensions for these grooves may be on the order of 0.07-0.4 mm (0.003-0.018 in.). Selection of an appropriate configuration for the channels may be guided by practical considerations including manufacturability, cost, strength, and other factors.

Figure 5A:
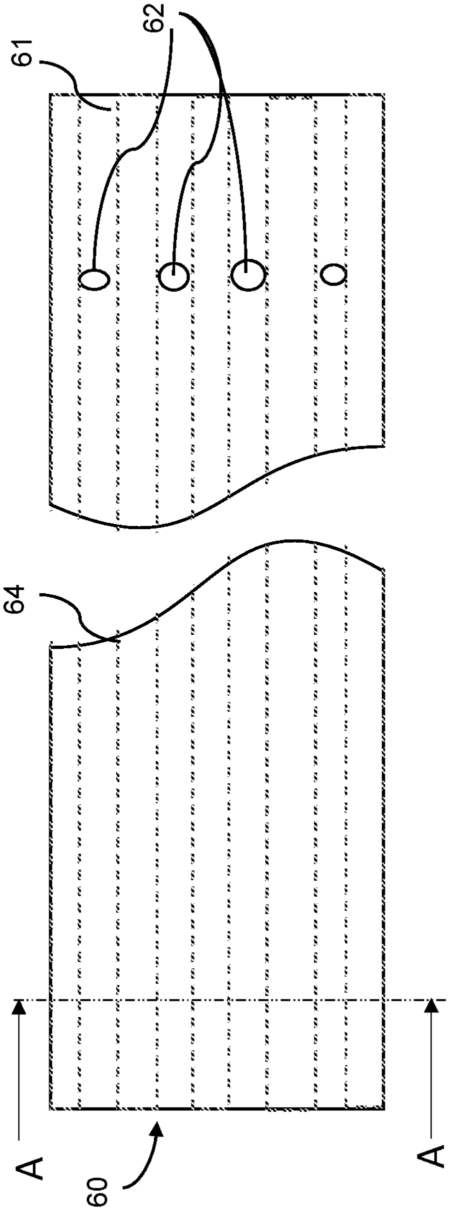
FIG. 5A is a side plan view of a sheath according to a second embodiment.
Figure 5B:
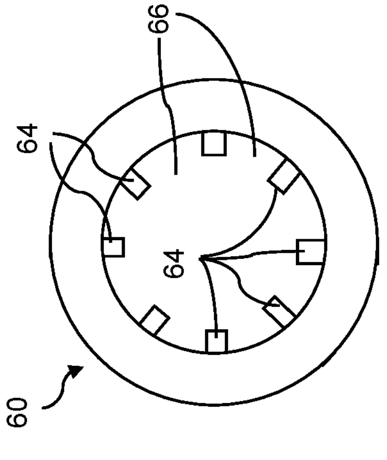
FIG. 5B is a cross-sectional view taken along line A-A of FIG. 5A.

FIGS. 5A-5B show an embodiment in which the inner surface of sheath 60 has a number of raised ribs 64 extending radially a short distance into the hollow center of the sheath. (Note that the ribs are shown exaggerated for illustrative purposes and will generally be less prominent in actual implementation.) While rectangular ribs are shown in the figure, the ribs 64 may have a variety of cross-sectional shapes including square or rectangular, triangular, curved, polygonal, or combinations thereof. The spaces 66 defined between adjacent ribs act as channels through which air/media can be transported along the length of the sheath. The depths of the channels will be optimized to the size of air bubbles or contrast media to enhance ultrasound visualization.

In some embodiments, the corresponding needle may have a continuous surface (non-grooved) outer diameter that closely fits within the spacing between opposing ribs 64. The ribs may extend down the entire length of sheath 60, so that the air/media exits the distal end 61 of the sheath through the multiple gaps 66 defined by the ribs. In the illustrated example, In another implementation, the needle shown in FIGS. 4A-4B can be combined with sheath 60, and optional openings 62, can be included so that the air/fluid is released through the openings to form bubbles (or other echogenic features) near the distal end 61.

Figure 6B:
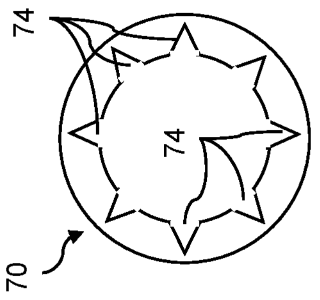
FIG. 6B is an end view of the distal end of the sheath of FIG. 6A.
Figure 6A:
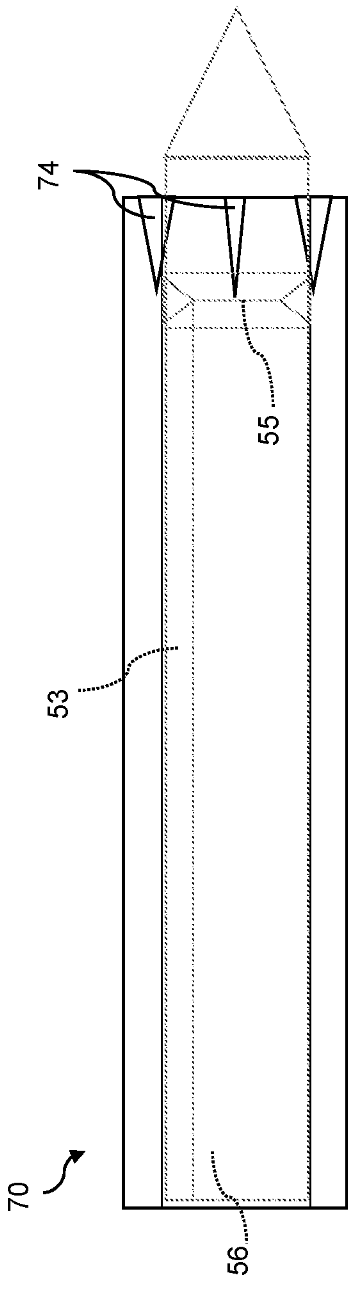
FIG. 6A is a side plan view of a sheath according to a third embodiment.

FIGS. 6A-6B illustrate still another embodiment of sheath 70 in which longitudinal tapered grooves 74 are formed on the sheath's inner surface near the distal end. As shown, the needle of FIGS. 4A-4B is shown in dashed lines to illustrate the alignment between needle channel 55 and the starting ends of grooves 74. In this combination, air/media fluid introduced into the sheath 70 is transported longitudinally along channel 53, enters intersecting channel 55 to be distributed to grooves 74 and carried out the distal end of sheath 70. The depths of the grooves 74 will be optimized to attain the desired the size of bubbles or media to enhance ultrasound visualization.

Figure 7:
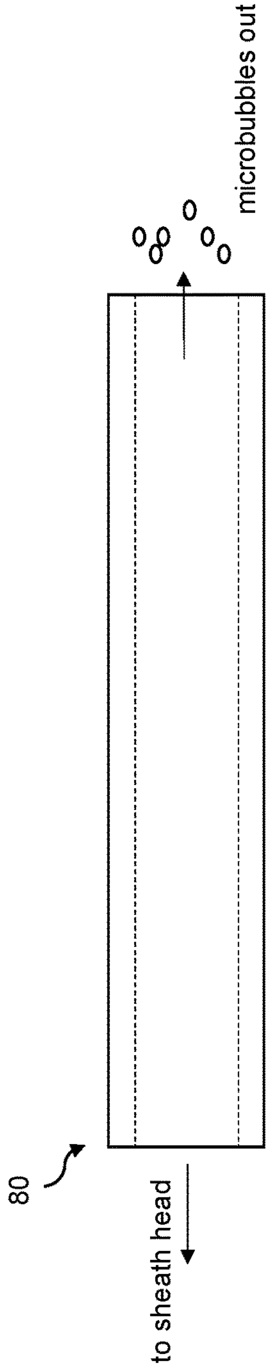
FIG. 7 is a side plan view of a sheath according to a fourth embodiment of the invention.

The embodiments shown in FIGS. 7 and 8A-8D induce the break-up of the fluid into bubbles by way of features of the needle shape and/or surface, without relying in variations in the sheath surfaces. FIG. 7 illustrates sheath 80, which is a simple hollow cylinder or tube with smooth inner and outer surfaces. As described with reference to FIGS. 1A and 1D, the sheath is dimensioned to closely receive the needle in a way that the needle can be inserted and withdrawn smoothly, to avoid binding or other resistance that could cause the assembly to move unintentionally. The proximal end of sheath 80 will mate with sheath head, as shown in FIG. 1D.

Figure 8A:
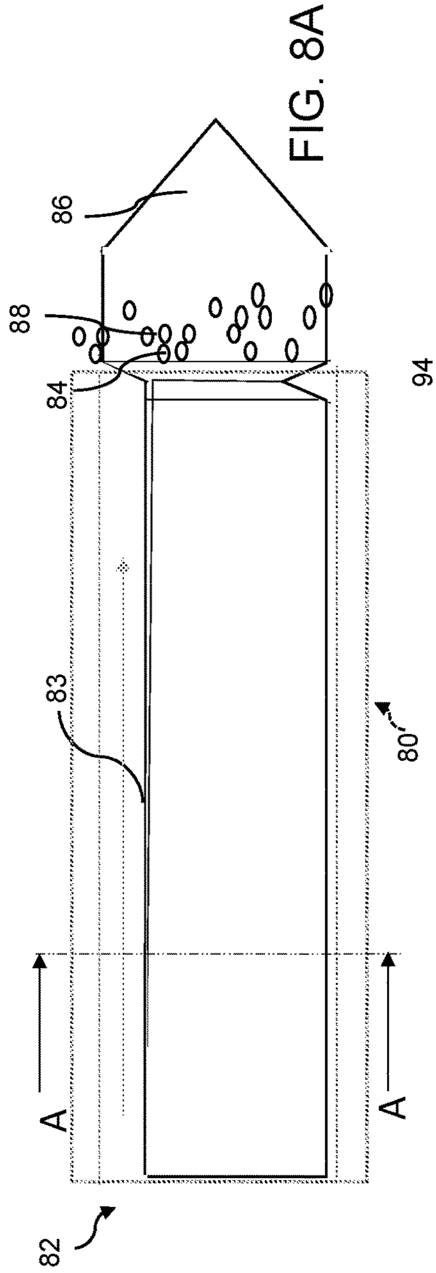
FIG. 8A is a side plan view of a sheath according to a fifth embodiment.
Figure 8B:
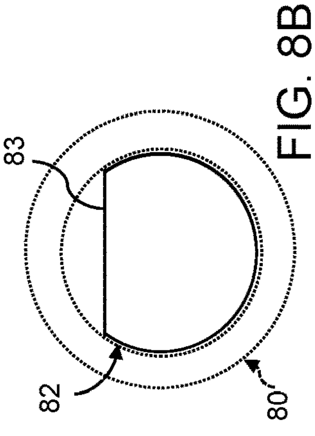
FIG. 8B is a cross-sectional view taken along line A-A of FIG. 8A.

Needle 82 shown in FIGS. 8A and 8B has a flattened channel 83 formed along the partial length of the needle so that it intersects annular channel 84 near the distal end of the needle. When needle 82 is inserted into sheath 80 (shown for reference with dashed lines), flattened channel 83 defines a pathway for air/fluid to be transported to the distal end of the assembly. When the air/media reaches annular channel 84, the transition to the fully rounded cross-section of the needle near distal end 86 causes the air/fluid to break up into bubbles 88, which are released at the end of sheath 80.

Figure 9A:
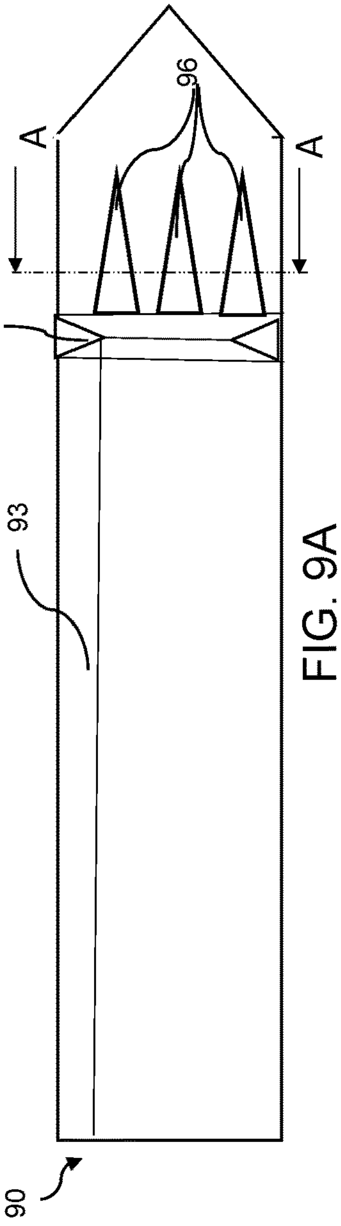
FIG. 9A is a side plan view of a sheath according to a sixth embodiment.
Figure 9B:
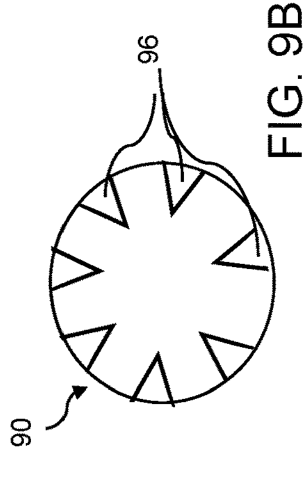
FIG. 9B is a cross-sectional view taken along line A-A of FIG. 9A.

FIGS. 9A-9B illustrate another embodiment of the needle that can be used with sheath 80, or with any other sheath embodiment. Needle 90 has a similar construction to that of needle 56 (FIG. 4A) with a longitudinal channel 93 running most of the length of the needle to transport the air/media within the spacing between the sheath inner surface and the needle outer surface. Channel 93 intersects annular channel 94, causing the air/media to be directed into channel 94. At the distal edge of channel 94 is an array of longitudinally-extending tapered grooves 96 that take the air/media from channel 94, convert it into bubbles and direct the bubbles toward the distal end of the needle. The dimensions and shape of the grooves 92 at the distal end of the needle can be optimized to the size of the bubbles to enhance ultrasound visualization.

The following examples provide illustrative descriptions of the methods of use of the inventive assembly Example 1: Efficacy and Feasibility Testing/Confirmation A prototype design of the needle/sheath assembly was built and tested to determine the function and efficacy of the system. A piece of meat, a 3-pound chuck roast, with a hollow interior area representing the renal calyx was used to simulate the function of the current device in a clinical environment. A BK Medical (Herlev, Denmark) imaging system with a multi-array probe was used for ultrasound visualization and guidance. A water-based hydrogel was used between the probe and the meat.

The guidance of the invention into the cavity of the roast was complicated by the reverberation and reflection of the needle as it passed through the meat. This phenomenon creates multiple images of the needle, making it difficult determine which image is the real needle image and its location in relationship to identifiable landmarks. Referring to FIG. 1D, air was injected through port 19 and into chamber 14 of the sheath head 13 at the proximal end of the sheath. The length of the needle 21 had been filed to create a channel along the interior of the sheath to allow passage of the air from the chamber 14 to the distal end of the sheath located in the meat. The end of the "real" needle, which extended a short distance beyond the end of the sheath, was immediately visible as the air bubbles generated at the distal end of the sheath were visible as bright circular objects emanating from the end of the sheath and creating shadowing to the air bubbles. The position of the end of the sheath in the cavity in the meat was confirmed by removing the needle from the sheath and inserting a wire through the sheath and into the cavity. The meat was then cut open to expose the cavity and physically confirm the presence of the wire in the cavity.

Example 2: Method of Use

Figure 10:
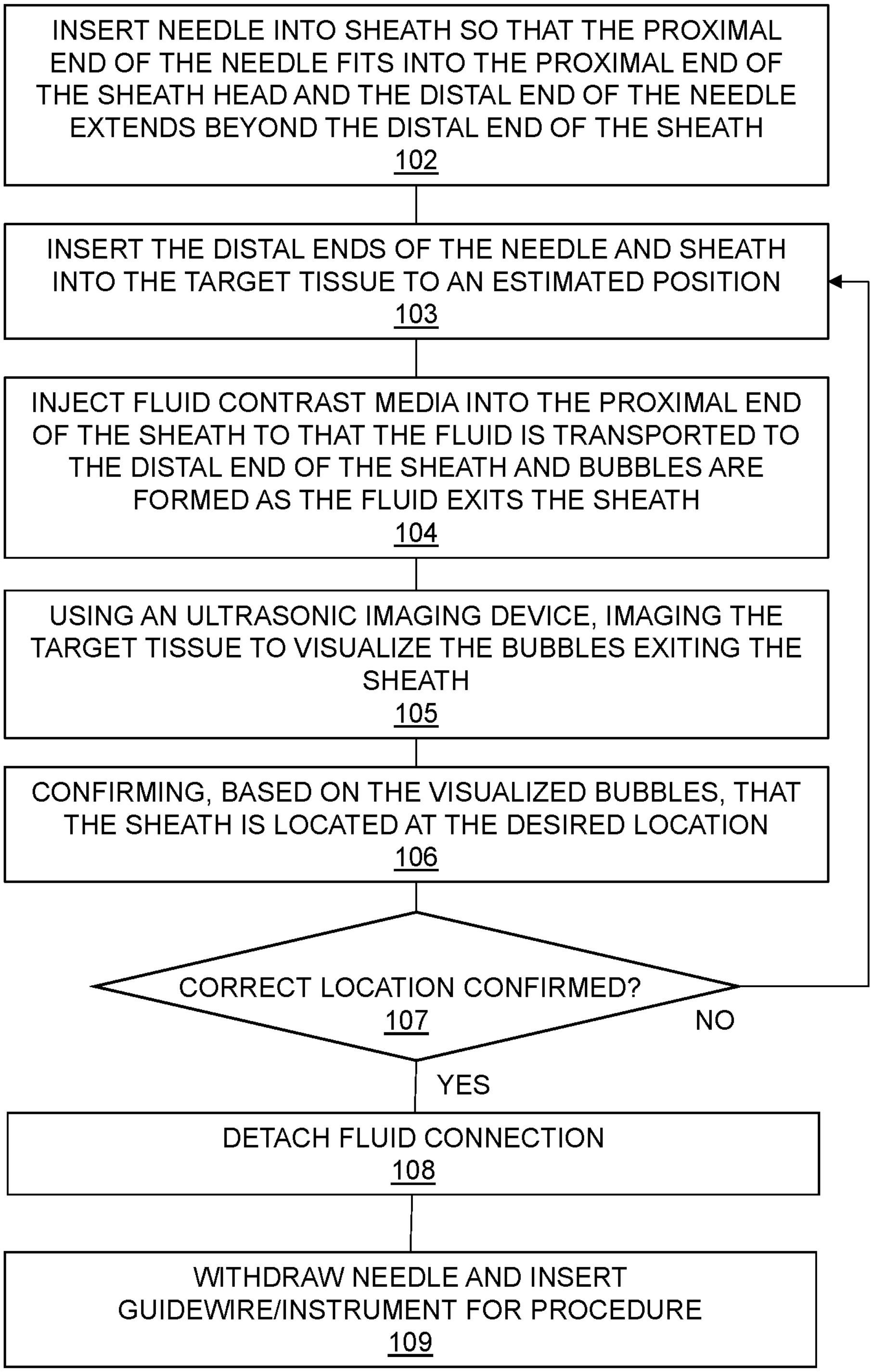
FIG. 10 is a flow diagram of an exemplary procedure using the inventive assembly.

FIG. 10 provides an exemplary sequence for use of an embodiment of the inventive assembly in a procedure involving tissue puncture. Numerical references are to elements of the assembly refer to FIG. 1D.

In step 102, the user (or an assistant) inserts the needle 21 into sheath head 13 and sheath 12 until needle stopper 22 fits into bore 17 and the distal end 25 of needle 12 extends from the sheath tip. In step 103, the user inserts the needle and sheath through the exterior of the target tissue to the approximate location of the desired treatment. A skilled practitioner would be expected to be relatively accurate in the placement at this point, however, the object of the invention is to enhance accuracy of the ultimate positioning for the procedure, and to make it easier for a less experienced user to accurately position the device. Preparations are made for ultrasonic imaging of the target area, and in step 104, an injector 30 connected to a fluid source is attached to port 19 of sheath head 13 and the fluid is injected into sheath head 13 so that it is forced into the transport channel between the needle 21 and the inner surface of sheath 12 to the distal end of sheath 12 where bubbles are formed. Concurrently with step 104, the imaging procedure of step 105 begins to visualize the appearance of bubbles from the end of the sheath. Using this visualization, the user confirms in step 106 that the sheath and needle are positioned at the desired location. In step 107, if the correct positioning is not indicated by the ultrasound image, the user may move and/or partially retract the assembly and repeat step 103 to reposition the assembly based on the location information obtained during initial imaging step 105. Steps 106 and 107 are repeated if necessary until the correct position is achieved. In step 108, the fluid connection is detached and the tubing withdrawn to clear the area of obstacles not required for the procedure. For procedures in which additional actions are to be performed, for example, if a nephroscope is to be inserted, or an ultrasonic or laser probe is to be used for inserted for treatment, in step 109, the needle is withdrawn and a guidewire or other instrument may be inserted into the sheath over which other instruments may be passed into the renal calyx to perform other actions.

The inventive assembly defines a transport channel between a needle concentrically and removably disposed within a sheath. Features are formed within the channel induce break up of air or contrast media that has been introduced into the transport channel to form bubbles or other echogenic areas. The bubble-inducing features may be formed in the needle, the sheath, or a combination thereof. The embodiments described herein provided illustrative examples of different combinations of features that can be used to achieve the object of generating bubbles or echogenic features for visualization using ultrasonic imaging techniques. The different combinations of components and features described herein are not intended to be limiting, and as will be readily apparent to those in the art, components described with reference to one combination may be utilized in combination with other components without deviating from the overall invention.

The invention claimed is:

1. An assembly for facilitating ultrasonic visualization of positioning of a needle inserted into tissue, the needle having a needle length, the assembly comprising:

a sheath having a sheath length and configured for concentrically receiving the needle to form a substantially fluid tight fit between an outer surface of the needle and an inner surface of the sheath, the sheath having a sheath head disposed at a proximal end configured for introducing fluid into a transport channel defined between one or a combination of the outer surface of the needle and the inner surface of the sheath, wherein the transport channel comprises features configured for inducing formation of ultrasonically visible features at a distal end of the sheath; and a fluid source in fluid communication with the sheath head for introducing fluid under pressure.

2. The assembly of claim 1, wherein the transport channel comprises at least one longitudinal channel formed in the inner surface of the sheath.

3. The assembly of claim 2, wherein the at least one longitudinal channel comprises a plurality of longitudinal channels extending along the sheath length.

4. The assembly of claim 3, wherein the plurality of longitudinal channels are defined by ribs extending radially inward from the inner surface of the sheath.

5. The assembly of claim 2, wherein the at least one longitudinal channel comprises a plurality of longitudinal channels shorter than the sheath length disposed near the distal end of the sheath.

6. The assembly of claim 2, wherein the sheath has a plurality of radial openings disposed therein near a distal end of the sheath.

7. The assembly of claim 1, wherein the transport channel comprises at least one longitudinal channel formed in an outer surface of the needle.

8. The assembly of claim 7, wherein the at least one longitudinal channel extends a partial length of the needle to intersect with an annular channel configured to direct the fluid radially outward from the needle.

9. The assembly of claim 8, wherein the annular channel is disposed at a position along the needle length corresponding to the distal end of the sheath.

10. The assembly of claim 8, wherein the annular channel is disposed at a position along the needle length that is less than the full sheath length, and wherein the sheath has a plurality of radial openings disposed to align with the annular channel.

11. The assembly of claim 8, wherein the annular channel is disposed at a position along the needle length that is less than the full sheath length, and wherein the sheath has a plurality of tapered grooves formed on the inner surface, each groove having a first end that aligns with the annular channel and a second end that extends to the distal end of the sheath.

12. The assembly of claim 8, further comprising a plurality of tapered grooves disposed near a distal end of the needle, wherein the plurality of tapered grooves extend distally from the annular channel.

13. The assembly of claim 7, wherein the at least one longitudinal channel is formed by flattening a side of the needle.

14. The assembly of claim 7, wherein the at least one longitudinal channel comprises at least one groove formed in the outer surface of the needle.

15. The assembly of claim 1, wherein the needle length is greater than the sheath length.

16. The assembly of claim 1, wherein the fluid is air or a contrast media suspension.

17. A method for visualizing positioning of a needle inserted into tissue, comprising:

inserting into a target tissue the assembly of claim 1;
introducing an echogenic media into the assembly; and
using an ultrasonic imaging instrument to generate an image of ultrasonically visible features at the distal end of the sheath.

18. An assembly for facilitating ultrasonic visualization of positioning of a needle inserted into tissue, the assembly comprising:

a sheath comprising a hollow tubing having a sheath length and a sheath end, the sheath having a sheath head disposed at a proximal end configured for introducing fluid into the sheath;

the needle concentrically disposed within the sheath to form a substantially fluid tight fit between an outer surface of the needle and an inner surface of the sheath, wherein a transport channel is formed between one or a combination of the outer surface of the needle and the inner surface of the sheath, wherein the transport channel comprises features configured for inducing formation of ultrasonically visible features at the sheath end; and a fluid source in fluid communication with the sheath head for introducing fluid under pressure.

19. The assembly of claim 18, wherein the transport channel comprises at least one longitudinal channel formed in the inner surface of the sheath.

20. The assembly of claim 19, wherein the at least one longitudinal channel comprises a plurality of longitudinal channels extending along the sheath length.

21. The assembly of claim 20, wherein the plurality of longitudinal channels are defined by ribs extending radially inward from the inner surface of the sheath.

22. The assembly of claim 19, wherein the at least one longitudinal channel comprises a plurality of longitudinal channels shorter than the sheath length disposed near the sheath end.

23. The assembly of claim 19, wherein the sheath has a plurality of radial openings disposed therein near the sheath end.

24. The assembly of claim 18, wherein the transport channel comprises at least one longitudinal channel formed in an outer surface of the needle.

25. The assembly of claim 24, wherein the at least one longitudinal channel extends a partial length of the needle to intersect with an annular channel configured to direct the fluid radially outward from the needle.

26. The assembly of claim 25, wherein the annular channel is disposed at a position along the needle length corresponding to the sheath end.

27. The assembly of claim 25, wherein the annular channel is disposed at a position along the needle length that is less than the full sheath length, and wherein the sheath has a plurality of radial openings disposed to align with the annular channel.

28. The assembly of claim 25, wherein the annular channel is disposed at a position along the needle length that is less than the full sheath length, and wherein the sheath has a plurality of tapered grooves formed on the inner surface, each groove having a first end that aligns with the annular channel and a second end that extends to the sheath end.

29. The assembly of claim 25, further comprising a plurality of tapered grooves disposed near a distal end of the needle, wherein the plurality of tapered grooves extend distally from the annular channel.

30. The assembly of claim 24, wherein the at least one longitudinal channel is formed by flattening a side of the needle.

31. The assembly of claim 24, wherein the at least one longitudinal channel comprises at least one groove formed in the outer surface of the needle.

32. The assembly of claim 18, wherein the needle length is greater than the sheath length.

33. The assembly of claim 18, wherein the fluid is air or a contrast media suspension.

34. A method for visualizing positioning of a needle inserted into tissue, comprising:

inserting into a target tissue the assembly of claim 18;
introducing an echogenic media into the assembly; and
using an ultrasonic imaging instrument to generate an image of ultrasonically visible features at the sheath end.

* * * * *